United States Patent [19]
Mitsumaki et al.

[11] Patent Number: 5,876,670
[45] Date of Patent: Mar. 2, 1999

[54] MULTI-ITEM ANALYZER HAVING PLURALITY OF ANALYZING MODULES

[75] Inventors: Hiroshi Mitsumaki, Mito; Ryuichi Kodama, Hitachinaka; Tomonori Mimura, Nishiibaraki-gun, all of Japan

[73] Assignee: Hitachi, Ltd., Tokyo, Japan

[21] Appl. No.: 858,691

[22] Filed: May 19, 1997

[30] Foreign Application Priority Data

May 20, 1996 [JP] Japan ..................................... 8-124338

[51] Int. Cl.⁶ .............................. G01N 1/18; G01N 27/00
[52] U.S. Cl. ........................... 422/65; 422/67; 422/82.01; 436/48
[58] Field of Search ........................... 422/65, 67, 82.01; 436/47, 48, 50

[56] References Cited

U.S. PATENT DOCUMENTS 5,087,423  2/1992  Ishibashi .................................... 422/65
5,614,415  3/1997  Markin ....................................... 436/47

FOREIGN PATENT DOCUMENTS 63-271164  11/1988  Japan .
3-180763   8/1991   Japan .
6-27745    4/1994   Japan .

*Primary Examiner*—Jan Ludlow
*Attorney, Agent, or Firm*—Fay, Sharpe, Beall, Fagan, Minnich & McKee

[57] ABSTRACT

A multi-item analyzer includes a first analyzing module for performing analysis items having a larger request in number arranged in the upstream side of a transporting line, and a second analyzing module for performing analysis items having a smaller request in number arranged in the downstream side. A sample sampling position for the analyzing module in the upstream side is provided on the transporting line, and a sample sampling position for the analyzing module in the downstream side is provided on a rack receiving area.

8 Claims, 1 Drawing Sheet

MULTI-ITEM ANALYZER HAVING PLURALITY OF ANALYZING MODULES

BACKGROUND OF THE INVENTION

The present invention relates to a multi-item analyzer, and more particularly to a multi-item analyzer in which a plurality of analyzing modules are arranged along a transporting line of a sample rack.

As for a multi-item analyzer for analyzing many samples requested to inspect a plurality of analysis items, for instance, Japanese Patent Application Laid-Open No.6-27745 discloses an automatic analyzer in which a plurality of analyzing units are arranged along a rack transporting unit for transporting a sample rack containing a sample. The automatic analyzer of this kind is suitable for multi-item and multi-sample processing, and when one analyzing unit is insufficient for performing processing, by providing a plurality of analyzing units many analysis items can be processed by distributing them to the plurality of analyzing units.

However, since analysis items requested for each sample are made for a choice depending on the state of a disease of a patient, there is a disadvantage in making useless measurements of unnecessary analysis items when all analysis items are evenly measured using an automatic analyzer which has a sample processing capacity per unit time. As for an automatic analyzer improving the efficiency of such a processing capacity, for instance, Japanese Patent Application Laid-Open No.3-180763 discloses an automatic analyzer of which the efficiency of processing capacity is improved in that all analysis items are classified into groups and the analysis items are allocated to individual analyzing modules so that an integrated value of a number of analyses to be requested for each of the groups may become the same.

SUMMARY OF THE INVENTION

There are two standards for evaluating processing capacity of an automatic analyzer. The first is how fast all samples are processed and the second is how fast a result of a specified sample is reported when the result of the specified sample is taken into consideration. It is not sufficient when only one of the two evaluation standards is satisfied. If processing of samples for 1000 patients takes 5 hours and the first result can be obtained 4 hours after starting the processing, diagnostic service will be stagnated for that period. On the other hand, if the first result among the samples for the 1000 patients can be obtained 10 minutes after starting the processing and the last result is obtained 10 hours after starting the processing, it is impossible to complete the diagnostic service for all of the patients within one day. In other words, the automatic analyzer needs to satisfy the two requirements of total processing capability expressed by samples/hour and average reporting time expressed by hour.

In each of the above-mentioned examples of the conventional technology, although consideration is given to improving the efficiency of the total processing capability, it cannot be said that a sufficient solution for the average reporting time is obtained. For instance, in a case where there are arranged two analyzing modules A and B from an inlet portion side of samples, it is thought that samples having an analysis request concentrated only on the analyzing module A, samples having an analysis request concentrated only on the analyzing module B and samples having an analysis request separated to both of the analyzing modules A and B are randomly mixed, depending on specific analysis items requested by each of the samples. Now, providing that the analyzing module B is in a stand-by state and a sample having an analysis request concentrated only on the analyzing module B is waiting behind a sample having an analysis request concentrated only on the analyzing module A, it is possible to improve the processing capacity and thereby to shorten the reporting time if the former sample can reach the analyzing module B by passing the latter.

In clinical inspection in the past, all samples are analyzed on all of the determined analysis items of, for instance, 12 items or 16 items. At present, in a first inspection upon entering the hospital, it is requested to perform screening inspection in which all analysis items are analyzed overall. However, as a diagnosis is confirmed, the analysis items are limited to items related to the diagnosed disease. In a case of liver disease, liver function inspection items are requested, and in a case of kidney disease, kidney function inspection items are requested. There are about 40 typical analysis items in biochemical inspection. Frequencies of the analyses of the biochemical inspection requested to a clinical inspection section become as follows when they are listed in order of magnitude by item. In most cases, the pattern of the frequencies is that the request frequencies are largest in the top three items, then decrease at a constant ratio up to nearly the twentieth largest item, and are small from the twenty-first largest item to the fortieth largest item. That is, passing between the samples occurs not so frequently in the top-ranked items having large request frequencies, but passing between the samples frequently occurs in the lower-ranked items having small request frequencies.

An object of the present invention is to provide a multi-item analyzer in which the average processing speed is improved using a plurality of analyzing modules and the reporting time of the analysis measuring results can be shortened.

The present invention is applied to a multi-item analyzer comprising a transporting line for transporting a sample rack mounting plural vessels respectively accommodating a sample liquid, a sample supplying device for supplying said sample rack on said transporting line, a first analyzing module provided along said transporting line, having a first sampling mechanism for sampling said sample liquid accommodated in said vessel mounted on said sample rack and a second analyzing module provided along said transporting line and disposed after said first analyzing module, having a second sampling mechanism for sampling said sample liquid accommodated in said vessel mounted on said sample rack.

The present invention is characterized by that said first sampling mechanism of the first analyzing module directory samples said sample liquid accommodated in said vessel mounted on said sample rack on said transporting line, and said second analyzing module has a rack receiving area for temporarily receiving said sample rack from said transporting line, and said second sampling mechanism samples said sample liquid accommodated in said vessel mounted on said sample rack on said rack receiving area.

In a preferable embodiment of the present invention, the second analyzing module comprises a pipetter for pipetting a reagent into a sample liquid in a reaction portion sampled from a vessel on the sample rack received in the rack receiving area. Further, the rack transferring unit selectively transfers a sample rack to be analyzed by the second analyzing module to the rack receiving area corresponding to an analysis item requested by a control device to sample accommodated in a vessel mounted on each of the sample racks. Particularly, it is preferable that an electrolytic measuring module is employed as the first analyzing module. Furthermore, in addition to the general sample supplying portion, the multi-item analyzer further comprises an urgent sample supplying portion for supplying an urgent sample rack containing a sample to be urgently analyzed to the transporting line preferentially to a sample rack supplied from the general sample supplying portion. By doing so, urgent analysis can be easily performed.

DETAILED DESCRIPTION OF THE PREFERRED EMBODIMENTS

Embodiments based on the present invention will be described in detail below, referring to the accompanying drawings. In a first embodiment of FIG. 1 and a second embodiment of FIG. 2, a rack loading five sample containers such as test-tubes accommodating sample liquid is used as a sample rack. However, the sample rack is not limited to such a rack, but it is possible to employ anything in which a plurality of sample containers can be arranged. A label having an identification code such as bar code is attached on the sample container, the bar code or the like is read by a code reader such as a bar code reader upon transporting the sample rack and each sample ID is recognized by a control unit containing a computer. The sample rack itself also has a bar code or a plurality of light-pass perforations and the control unit recognizes the sample rack number from a read result of the bar code by the reader. A body liquid such as blood or urine is contained in the sample container as a sample.

Figure 1:
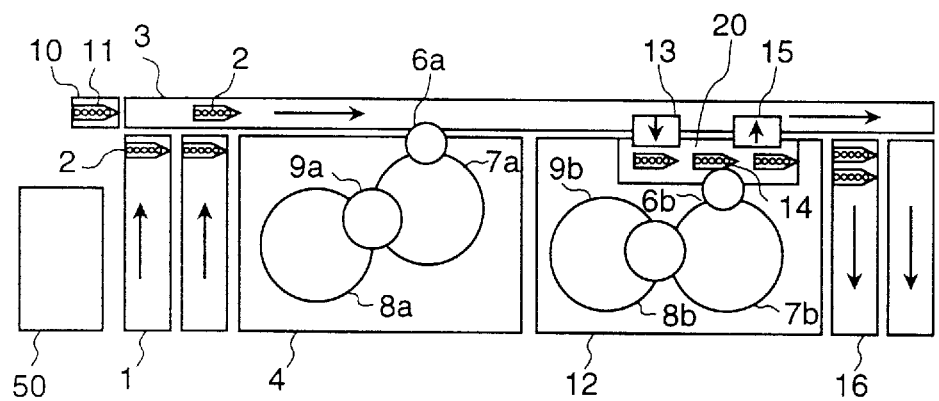
FIG. 1 is a view illustrating the construction of a first embodiment in accordance with the present invention.

Referring to FIG. 1, a first analyzing module 4 and a second analyzing module 12 are arranged along a sample rack transporting line 3 for a sample rack. In the second analyzing module 12 arranged in the downstream side of the transporting line 3, there is formed a rack receiving area 20 for temporarily storing the sample rack 2 from the transporting line 3 in order to sample by pipetting the sample. However, there is no such rack receiving area provided in the first analyzing module 4 arranged in the upstream side of the transporting line 3, so a sample is directly pipetted from a sample rack stopped for a brief period of time on the transporting line 3 into the first analyzing module 4. A sampling mechanism 6a having a pipette nozzle serves as a sample pipetter which adds the sample pipetted from the sample rack on the transporting line 3 into a reaction container of a reaction disk 7a having reaction containers arranged along its circular periphery. The sample is mixed with a reagent corresponding to an analysis item and the reaction liquid produced in the reaction container is optically measured using a multi-wavelength photometer attached to the reaction disk 7a.

Sample racks 2 containing general samples are orderly placed on a sample supplying portion 1 consisting of two rack trays to be transferred toward the transporting line 3 one-pitch by one-pitch based on an order generated from a control unit 50. All the sample racks 2 mounted on the transporting line 3 from the sample supply portion 1 pass through the sampling position for the first analyzing module 4 on the transporting line. On the other hand, the sample storing portion 16 consists of two rack trays, and receives sample racks 2 after completion of sample pipetting from the transporting line 3 and successively places the sample racks on the tray based on an order generated from the control unit 50. The transporting line 3 comprises a belt driven by a pulse motor to be rotated from the upstream side to the downstream side based on an order generated from a control unit 50. An intermittent operation of the transporting line 3 which repeats stopping of the transporting line 3 in front of the respective analyzing modules and transporting to the next analyzing module or the sample storing portion is controlled by an order generated from the control unit 50.

The second analyzing module 12 has the rack receiving area 20 for temporarily receiving the sample racks. A sample rack 2 stopped at a receiving position on the transporting line 3 is transferred to the rack receiving area 20 using a rack transferring unit 13 for receiving sample racks based on the order generated from the control unit 50. The received sample rack is moved up to a sampling position 14.

At the sampling position on 19, using a sampling mechanism 6b with a pipetter having a pipette nozzle, a sample on the sample rack is pipetted and maintained in the pipette nozzle. Then, the sample is ejected from the pipette nozzle into a reaction container (which is not shown in the figures) on a reaction disk 7b. The sample rack after completion of sample pipetting is moved to a position for sending-out sample rack in the rack receiving area 20 to be returned on the transporting line 3 using a rack transferring unit 15 for sending-out sample rack.

Here, the sample rack finishing to be sampled into the first analyzing module 4 is controlled so as to pass through in front of the second analyzing module 12 by checking that no sample rack does not return on the transporting line 3 from the rack receiving area 20. In a0 case where a sample rack passes through in front of the second analyzing module 12 just when a sample rack returns on the transporting line 3, the sample rack is controlled to pass through in front of the second analyzing module 12 after the sample rack returns on the transporting line 3.

As to each of the rack transferring units 13, 15, an arm for holding the sample rack or a rack pushing mechanism for pushing the sample rack is used. Only sample racks containing a sample having a requested analysis item to be analyzed by the second analyzing module 12 are stopped at the receiving position on the transporting line corresponding to the rack transferring unit 13. The other sample racks are transported so as to pass by in front of the rack transferring unit 13.

A predetermined amount of the sample extracted from a sample container placed at a first position on the sample rack 2 stopped on the transporting line 3 is pipetted into a reaction container of the reaction disk 7a, and then a predetermined amount of a reagent is pipetted from a reagent bottle placed on a reagent disk 8a into the reagent container using a reagent pipetting mechanism 9a to react with the sample. After a certain time period of reaction in the reaction container, the reaction liquid is measured using a photometer, not shown, and the result is output as a measured result for one of the analysis items. When one of the analysis items set to the analyzing module 4 is further requested to be sampled again the sample is placed on the first position on the sample rack and the above sampling operation is repeated. Furthermore, a similar operation is repeated for a sample placed in another second position on the sample rack. Thus, the operations are repeated for all the samples on the sample rack until sampling operations for the many analysis items set to the analyzing module 4 are completed.

An urgent sample supplying portion 10 is provided in one end of the transporting line near the sample supplying portion 1. If an urgent sample rack 11 is placed at the urgent sample supplying portion 10 when a sample rack is placed at the sample supplying portion 1, the urgent sample rack 11 placed at the urgent sample supplying portion 10 is transferred to the transporting line 3 in preference to the general sample rack placed at the sample supplying portion 1.

For a sample rack 2 after completion of sample sampling at the analyzing module 4, the computer of the control unit 50 judges whether or not the analysis items of the second analyzing module 12 are requested to be performed to all of the samples placed on the sample rack. Whenever any one of the analysis items is requested to be performed, the sample rack is moved to a position corresponding to the analyzing module 12, and received inside the rack receiving area 20 of the analyzing module 12 using the rack transferring unit 13, and moved to a sampling position 14 in the module. Then, a predetermined amount of the sample extracted using a sampling mechanism 6b is pipetted into a reaction container of the reaction disk 7b, and then a predetermined amount of a reagent is pipetted from a reagent bottle placed on a reagent disk 8b into the reagent container using a reagent pipetting mechanism 9b to react with the sample. After a certain time period of reaction in the reaction container, the reaction liquid is measured using a photometer, not shown, and the result is output as a measured result for one of the analysis items. When one of the analysis items of the analyzing module 12 is further requested to be performed to the sample placed on the first position on the sample rack, the above sampling operation is repeated. Furthermore, a similar operation is repeated to a sample placed in the second position on the sample rack. Thus, the operations are repeated for all the samples on the sample rack until sampling operations for the analysis items set to the analyzing module 12 are completed. The sample rack after completion of sample sampling at the analyzing module 12 is transported to the position for sending-out sample racks in the rack receiving area 20 and returned to the transporting line 3 using a rack transferring unit 15 to be transported to a sample storing portion 16. In this case, the processing type of the analyzing module 12 installed in the downstream may be either a random-access type in which the reaction containers are used at random or a multi-item parallel processing type in which each of the reaction containers is used by fixing a specified item.

On the other hand, after completion of sample sampling in the first analyzing module 4, if the sample rack does not have any request for analysis items of the second analyzing module 12, the sample rack is transported to the sample storing portion 16 through the transporting line 3 to be stored without stopping in front of the second analyzing module.

According to the embodiment of FIG. 1, after completion of sample samplings for performing analysis items having a larger request in number in the first analyzing module 4, the control unit 50 judges whether or not the analysis items of the second analyzing module 12 arranged in the downstream are requested to be performed. Since a sample rack is introduced into the inside of the second analyzing module 12 from the transporting line to perform sampling only when there is a request, a following sample rack not having any analysis item in the second analyzing module 12 may pass by the preceding sample rack. Therefore, it is possible to attain the effect to shorten the reporting time including the average processing speed of the sampling.

As many analysis items in one sample are requested to be analyzed in the first analyzing module 4, and very few analysis items are requested in the second analyzing module 12, the transporting line 3 should be controlled with precedence so as to stop and transport a sample rack sampled in the first analyzing module 4 having priority over the sample rack sampled in the second analyzing module 12, thereby transportation of the sample racks are more effectively performed.

Especially, in a first case when a sample rack is sampled only in the first analyzing module 4 and is not sampled in the second analyzing module 12, and in a second case when a sample rack is not sampled in the first analyzing module 4 and is sampled only in the second analyzing module 12, the transportation of the transporting line 3 is the most effective. That is, in the first case, the sample rack sampled in the first analyzing module 4 may be transported to the next position without being stopped so as to pass by the preceding sample rack in the second analyzing module 12. Furthermore, in the second case, the sample rack which sampled in the second analyzing module 12 do not stop a following sample rack. Thereby, it becomes possible to shorten the reporting time including the average processing speed in analyzing the sample.

The second embodiment will be described below, referring to FIG. 2. In this embodiment, the analyzing module installed in the uppermost stream is an electrolytic measuring module 17 which has a high requested frequency in clinical biochemical inspection. The electrolytic measuring module 17 does not have a rack receiving area. In the downstream side, a second analyzing module 26 and a third analyzing module 30 are arranged along the transporting line 3. The construction of the second and the third analyzing modules are the same as the construction of the analyzing module 12 in FIG. 1, and the second analyzing module 26 has a rack receiving area 21 and the third analyzing module 30 has a rack receiving area 22.

The electrolytic measuring module 17 has a diluting container and a flow cell. A sampling mechanism 24 serving as a sample sampling unit directory sucks and holds a sample for which an electrolytic measurement has been requested, from a sample rack 2 stopped at the sampling position on the transporting line 3 into the pipette nozzle in the sampling mechanism 24 and deliver to the diluting container in the electrolytic measuring module 17. A predetermined amount of a dilute liquid supplied by a dilute liquid supplying unit and a predetermined amount of the sample are mixed in the diluting container to form a dilute sample diluted to a predetermined ratio. This dilute sample is sucked by a sucking nozzle of a shipper mechanism an introduced to the flow cell, and the electrolytic components in the sample are measured. In this embodiment, ion selective electrodes for respectively measuring sodium, potassium and chlorine ions are arranged in the flow cell to measure these ion concentrations. If there is no sample for which an electrolytic measurement has been requested on a sample rack, sampling processing for the sample is not performed though the sample rack passes by the sampling position of the sampling mechanism 24.

As stated above, the sample racks 2 arranged in the sample supplying portion 1 is as transferred to the transporting line 3 and then transported to the electrolytic measuring module 17 installed upstream. In the electrolytic measuring module 17, there is provided a sampling mechanism 24 which can sample a sample directly from a sample rack on the transporting line. A sample extracted from the sample at the first position of the sample rack 2 stopped on the transporting line 3 is measured by the ion selective electrode, not shown, and the result is output as a measured result for the analysis item. When one of the analysis items of the electrolytic measuring module 17 is requested to be performed to the sample placed at the second position on the sample rack, the above sampling operation is repeated. Thus, the operations are repeated to all the samples on the sample rack until sampling operations are completed. The transporting line 3 is controlled to stop while the sampling is performed in the electrolytic measuring module 17.

An urgent sample supplying portion 10 is provided in one end of the transporting line. If an urgent sample rack is placed at the urgent sample supplying portion 10 when a sample rack is placed at the sample supplying portion 1, the urgent sample rack 11 placed at the urgent sample supplying portion 10 is transferred to the belt line in preference to the general sample rack placed at the sample supplying portion 1.

For the sample rack 2 after completion of sample sampling at the electrolytic measuring module 17, the computer of the control unit 50 judges whether or not the analysis items of the second analyzing module 26 are requested to be performed to all of the samples placed on the sample rack. Whenever any one of the analysis items is requested to be performed, the sample rack is moved to the analyzing module 26 by a moving of the transporting line 3 and stops. The stopped sample rack is received inside the rack receiving area 21 of the analyzing module 26 using the rack transferring unit 27 installed in the module, and moved to a sampling position 28 in the module. Then, a predetermined amount of the sample extracted using a sampling mechanism 6c is pipetted into a reaction container of the reaction disk 7c, and a predetermined amount of a reagent is pipetted from a reagent bottle placed on a reagent disk 8c into the reagent container using a reagent pipetting mechanism 9c to react with the sample. After a certain time period of reaction in the reaction container, the reaction liquid is measured using a photometer, not shown, and the result is output as a measured result for one of the analysis items. When one of the analysis items of the analyzing module 26 is further requested to be performed to the sample placed on the first position on the sample rack, the above sampling operation is repeated. Furthermore, a similar operation is repeated to a sample placed in the second position on the sample rack. Thus, the operations are repeated to all the samples on the sample rack until sampling operations for the analysis items set to the analyzing module 26 are completed.

The sample rack after completion of sample sampling at the second analyzing module 26 is transported to the position for sending-out sample racks in the rack receiving area 21 and returned to the transporting line 3 using a rack transferring unit 29 for sending-out sample racks. Further, the computer of the control unit 50 judges whether or not the analysis items of the third analyzing module 30 installed further downstream are requested to be performed to all of the samples placed on the sample rack. If any one of the analysis items is requested to be performed, the sample rack is moved to the analyzing module 30, and received inside the rack receiving area 22 of the analyzing module 30 using the rack transferring unit 31 installed in the analyzing module 30, and moved to a sampling position 32 in the module. Then, a predetermined amount of the sample extracted using a sampling mechanism 6d is pipetted into a reaction container of the reaction disk 7d, and a predetermined amount of a reagent is pipetted from a reagent bottle placed on a reagent disk 8d into the reagent container using a reagent pipetting mechanism 9d to react with the sample. After a certain time period of reaction in the reaction container, the reaction liquid is measured using a photometer, not shown, and the result is output as a measured result for one of the analysis items. The operations are repeated to all the samples on the sample rack until sampling operations for the analysis items of the analyzing module 30 are completed.

The sample rack after completion of sample sampling at the third analyzing module 30 is transported to a position for sending-out sample racks in the rack receiving area 22 and returned to the transporting line 3 using a rack transferring unit 33 for sending-out sample racks to be transported to a sample storing portion 16.

On the other hand, after completion of sample sampling in the electrolytic measuring module 17, if the sample rack does not have any request for analysis items of the second analyzing module 26 or the third analyzing module 30, and after completion of sample sampling in the second analyzing module 26, if the sample rack does not have any request for analysis items of the third analyzing module 30, the sample rack is transported to the sample storing portion 16 through the transporting line 3 without stopping in front of the analyzing module midway to be stored in the sample storing portion 16.

Figure 2:
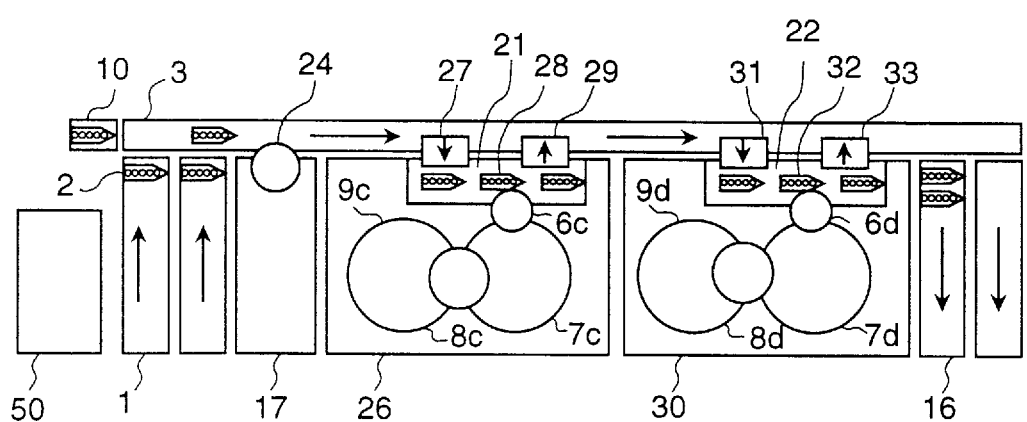
FIG. 2 is a view illustrating the construction of a second embodiment in accordance with the present invention.

According to the embodiment of FIG. 2, the electrolytic measuring module 17, particularly for analysis items having a larger request in number is arranged upstream as an analyzing module capable of sampling directly from a sample rack on the transporting line, and a plurality of analyzing modules capable of receiving a sample rack from the transporting line into the analyzing module are arranged in downstream. Thereby, it is possible to shorten the reporting time including the average processing speed, because the sampling in the downstream analyzing module does not restrain the moving of the sample rack in the upstream.

In each of the embodiments described above, working mechanism units for sample identification, sample bar code reading and cap opening of sample containers performed to all of the sample racks may be arranged in the upstream side along the transporting line. In this case, after performing the work to all of the sample racks, all of the racks pass through a sampling position on the transporting line corresponding to an analyzing module not having a rack receiving area, and then pass to an analyzing module having a receiving area arranged in the downstream side, it is determined whether or not the sample rack is received in the analyzing module depending on the measuring request for analysis items for each sample.

In each of the embodiment described above, a plurality of analyzing modules are arranged along the transporting line, an analyzing module installed in the upstream side is provided with a sample sampling position for analysis items having a larger request in number at a position on the transporting line where all of the sample racks must pass through, an analyzing module set to analysis items having a smaller request in number is arranged in the downstream side, the analyzing module arranged in the downstream side is provided with a sample handling unit which receives a sample rack from the transporting line into the analyzing module and returns the sample rack to the transporting line again after completion of sample pipetting work, and the control unit selectively judges whether or not a sample rack must be taken in the analyzing module arranged in the downstream side.

According to the present invention, the analyzing module for performing analysis items having a larger request in number is arranged in the upstream side of a transporting line and sampling processing of a sample can be performed directly from a sample rack on the transporting line. An analyzing module having a rack receiving area is arranged in the downstream side, and a sample rack requesting analysis items having a smaller request in number can be selectively taken in the rack receiving area depending on analysis items set to the analyzing module to perform sampling processing. Therefore, most of the sample racks among all of the sample racks supplied to the transporting line on which are performed sample sampling processing directly on the transporting line in connection with the analyzing module in the upstream, and accordingly the time for receiving the sample rack into the analyzing module may be reduced in the upstream. On the other hand, a sample rack having a sample corresponding to analysis items of a module is selectively taken in the analyzing module in the downstream. Therefore, while a preceding sample rack is taken and is being stored in the module, a following sample rack not having a measuring request for the analysis items can be transported by passing the preceding sample rack. Thereby, it is possible to shorten the reporting time including the average processing speed for all samples.

What is claimed is:

1. A multi-item analyzer comprising
   a transporting line for transporting a sample rack holding a plurality of vessels respectively accommodating a liquid sample therein,
   a rack supplying device for supplying said sample rack to said transporting line,
   a first analyzing module provided along said transporting line and having a sample receiving vessel mounted thereon,
   a second analyzing module provided along said transporting line downstream of said first analyzing module in a moving direction of said sample rack moved on said transporting line, and having a reaction disk with reaction containers mounted thereon, said second analyzing module having a rack receiving area provided with a sampling position where said liquid sample accommodated in at least one of said vessels on the said sample rack shifted from the transported line is sucked out,
   a first sampling mechanism for pipetting the liquid sample from at least one of said vessels held on said sample rack into said sample receiving vessel with a first pipette nozzle, while said sample rack is stopped at a first sampling position on said transporting line,
   a rack shifting device for shifting said sample rack from said transporting line to said receiving area of said second analyzing module,
   a second sampling mechanism for pipetting the sample liquid from at least one of the plural vessels held on said sample rack which is shifted to said second sampling position, into at least one of said reaction containers, after said sample rack is transported from the transporting line onto the rack receiving area, and
   a controller for controlling said transporting line so that a following sample rack on the transporting line passes beside said second analyzing module, while a preceding sample rack having passed said first sampling position is shifted to said rack receiving area.

2. A multi-item analyzer as defined in claim 1, wherein said rack shifting device comprises
   a first rack transferring device for transferring said sample rack from said transporting line onto an acceptable position of said rack receiving area, and
   a second rack transferring device for transferring said sample rack from an exit position of said rack receiving area onto said transporting line.

3. A multi-item analyzer as defined in claim 2, wherein said second rack transferring device is disposed downstream in a moving direction of said transporting line of said first rack transferring device.

4. A multi-item analyzer as defined in claim 1, wherein said controller includes means for controlling said transporting line so as to stop said sample rack on said transporting line at said first sampling position of said first analyzing module.

5. A multi-item analyzer as defined in claim 1, wherein said controller includes means for controlling said transporting line so that said liquid samples in said vessels on said sample rack are assigned so as to be analyzed at the first analyzing module, said sample rack is stopped at said first sampling position while said liquid sample is pippetted, and thereafter said sample rack is transferred downstream of said first analyzing module.

6. A multi-item analyzer as defined in claim 1, further comprising
   an urgent sample rack supplying device disposed near said rack supplying device for supplying an urgent sample rack holding a vessel accommodating a liquid sample therein, and wherein said controller includes control means which operate to supply said urgent sample rack ahead of a sample rack supplied from the rack supplying device.

7. A multi-item analyzer comprising
   a transporting line for transporting a sample rack holding at least one vessel accommodating a liquid sample therein,
   a rack supplying device for supplying said sample rack to said transporting line,
   an electrolytic measuring module provided along said transporting line and having a sample diluting vessel and a flow cell,
   a chemical analyzing module provided along said transporting line, disposed downstream of said electrolytic measuring module, and containing a reaction disk having a reaction container thereon, said chemical analyzing module having a rack receiving area provided with a second sampling position where said liquid sample in said vessel on said sample rack shifted from said transporting line is sucked out,
   a first sampling mechanism for pipetting said liquid sample from said vessel on said sample rack to said sample diluting vessel, while said sample rack is stopped at a first sampling position on said transporting line,
   a second sampling mechanism for pipetting said liquid sample from said sample rack on said second sampling position to said reaction container, after said sample rack is shifted from said transporting line to said rack receiving area, and
   plural ion selective electrodes for detecting ions in a diluted liquid sample introduced from said sample diluting vessel into said flow cell.

8. A multi-item analyzer as defined in claim 7, further comprising
   a controller having means for controlling said transporting line so that a following sample rack holding at least one vessel accommodating a liquid sample therein passes beside said chemical analyzing module, while said sample rack preceedingly transported through said first sampling position is shifted to said rack receiving area.

* * * * *